United States Patent [19]
Gordon

[11] 3,936,937
[45] Feb. 10, 1976

[54] TRANSPORT CASE FOR GNATHOLOGICAL APPARATUS AND GNATHOSTOMATIC APPLIANCES

[76] Inventor: Woodford W. Gordon, 121 Miraloma Drive, San Francisco, Calif. 94127

[22] Filed: Nov. 19, 1973

[21] Appl. No.: 417,073

[52] U.S. Cl. ..................................................... 32/1
[51] Int. Cl.² ......................................... A61C 19/00
[58] Field of Search.................. 206/373, 372, 329; 312/DIG. 33, 244, 201; 32/1

[56] References Cited
UNITED STATES PATENTS

| | | | |
|---|---|---|---|
| 2,685,363 | 8/1954 | Falk et al. | 312/DIG. 33 |
| 2,702,626 | 2/1955 | Nuttle | 312/DIG. 33 |

*Primary Examiner*—Robert Peshock
*Attorney, Agent, or Firm*—Robert Charles Hill

[57] ABSTRACT

A case for containing gnathological apparatus and gnathostomatic appliances for transport between an orthodontist and an orthodontic laboratory. A rugged reusable case that will withstand the rigors of shipment via mail or like carrier and that has interior thereof fasteners for removably and rigidly mounting gnathological apparatus and gnathostomatic appliances so that the same will not be damaged or altered during transport or shipment.

8 Claims, 6 Drawing Figures

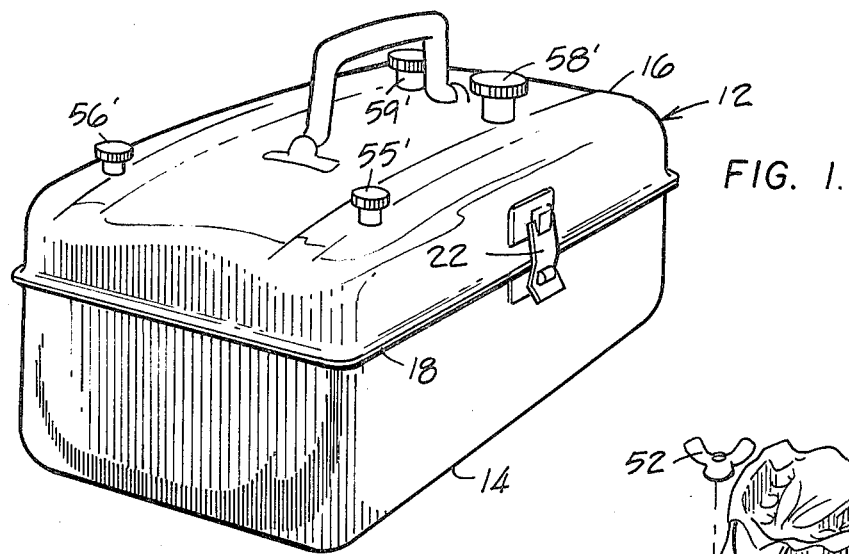
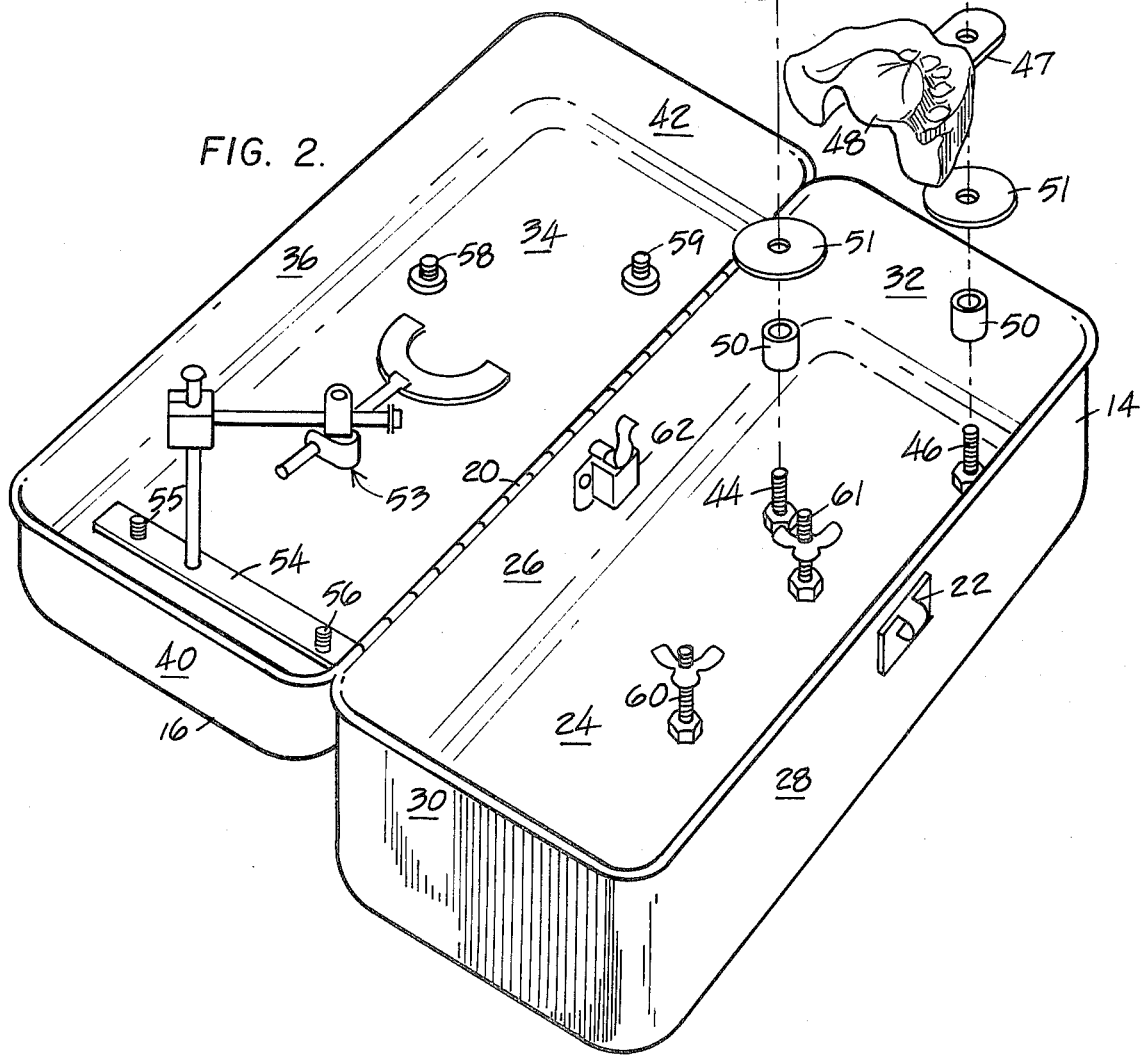

TRANSPORT CASE FOR GNATHOLOGICAL APPARATUS AND GNATHOSTOMATIC APPLIANCES

BACKGROUND OF THE INVENTION

In order to increase the time that an orthodontist can devote to direct treatment of patients, it is typical for certain appliances to be constructed to the orthodontists' specifications at an orthodontic laboratory. Typically, an orthodontic laboratory is located at some distance from the orthodontists' office so that models and/or impressions must be shipped by mail or like carrier. Heretofore it has been necessary for the orthodontist or the orthodontic laboratory to carefully wrap all materials and ship them in cardboard cartons which are then discarded. To produce an accurate positioner or like gnathostomatic appliance, it is essential that the laboratory be apprised of various measurements of the patient's jaw movements. Heretofore if such measurements were taken by the orthodontist on the patient by means of a face bow, pantograph or the like, the apparatus and measurements could not be transported to the laboratory except when reduced to numerical form and then transmitted to the orthodontic laboratory on paper. Reducing the measurements to written form is not only time-consuming for the orthodontist but affords an opportunity for transmission of erroneous measurements.

SUMMARY OF THE INVENTION

A principal object of the present invention is to provide a transport case for gnathological apparatus and gnathostomatic appliances that enhances the efficiency and accuracy with which an orthodontic laboratory can fill an order from an orthodontist. This object is achieved by providing a transport case which has facilities for firmly but removably retaining patient impressions and face bow apparatus which the orthodontist typically transmits to the laboratory and which retains plaster models and an articulator which the laboratory typically returns to the orthodontist for inspection and approval before the laboratory produces the final product, typically a gnathostomatic appliance for use by the patient. Because the case is of rugged exterior construction and because the appliances and apparatus are securely retained therein, breakage of the apparatus and appliances is virtually eliminated.

As used herein, gnathological apparatus refers to those instruments which measure placement of the teeth so that there are no interferences with proper mandibular movement. Gnathostomatic, on the other hand, pertains to movements of the jaw in relation to the teeth, muscles and nervous system.

A feature and advantage of the present invention is that by returning the articulator and models or molds to the orthodontist before the gnathostomatic appliance is finally fabricated, the orthodontist is afforded the opportunity to check the accuracy of the laboratory's work before final fabrication of the gnathostomatic appliance. When the orthodontist is satisfied that the set-up models and the articulator settings are as desired, he need only reinstall them interior of the case and return the case to the laboratory for final fabrication of the appliance.

Another feature and advantage of the present invention is that an entire pantograph apparatus can be transmitted between orthodontist and orthodontic laboratory. A pantograph is an instrument by which the orthodontist appraises and measures the relative position of the upper and lower jaws and movements thereof. This pantograph measurement dictates the relative position of the upper and lower teeth of the set-up models in conjunction with the patient's jaw movements. By providing a transport case which enables the pantograph, after it is adjusted in accordance with the patient's mandibular movements and jaw positions, to be transported to the laboratory, the orthodontist's time is saved and the likelihood of erroneous transcription and communication of measurements is virtually eliminated. Moreover, when the orthodontic laboratory has utilized the measurements recorded in the pantograph, the pantograph can be returned to the orthodontist in the same case with the models so that the set-up can be thoroughly checked by the orthodontist before final fabrication of the gnathostomatic appliance is completed.

BRIEF DESCRIPTION OF THE DRAWINGS

In the accompanying drawings:

FIG. 1 is a perspective view of a transport case of this invention in a closed position;

FIG. 2 is a perspective view of the transport case in an opened condition with a face bow and upper and lower impressions therein;

DESCRIPTION OF THE PREFERRED EMBODIMENTS

Figure 3:
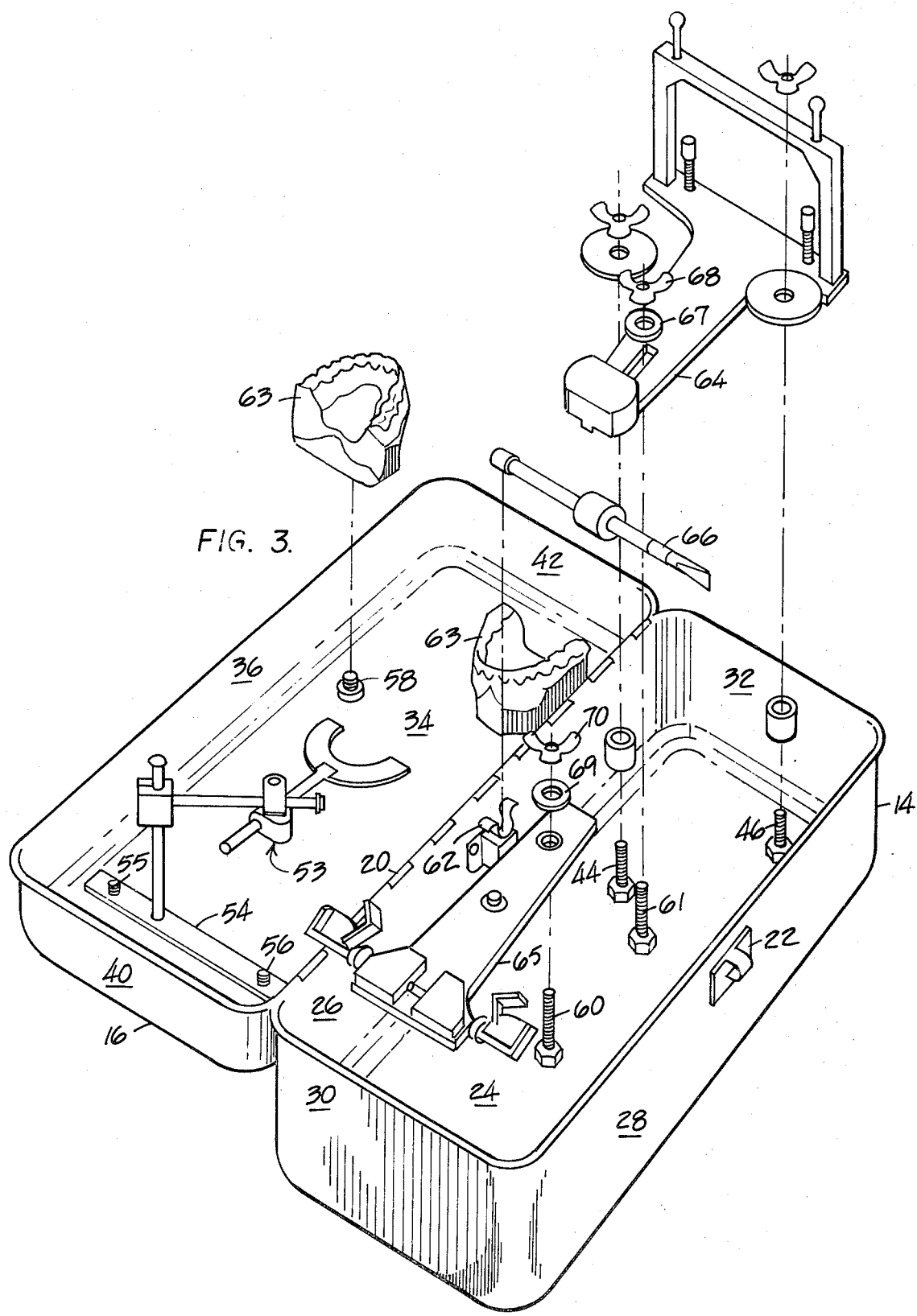
FIG. 3 is a perspective view of the case with the face bow, models and articulator, as would be transported by the laboratory to the orthodontist for checking before fabrication of the gnathostomatic appliance.

Referring more particularly to the drawings, reference numeral 12 indicates a case formed or rigid material such as steel, fiber reinforced plastic, or the like. Case 12 has a bottom portion 14 and a cover portion 16 which fit together along a parting line 18. At one side of the case along parting line 18 there is a hinge joint 20 and at the opposite side of the case is a locking mechanism such as a hasp 22.

The parallelepiped form of case 12 is merely exemplary of any suitable shape. In this particular embodiment, bottom section 14 includes a bottom wall 24, side walls 26 and 28 and end walls 30 and 32, which walls are rigidly joined together and are typically integral with one another. Top section 16 includes a top wall 34, side walls 36 and 38 and end walls 40 and 42, which are formed rigid with one another and are preferably integral with one another. The bottom and cover portions of the case are typically of similar size so that they form a relatively tight joint along parting line 18 when in the closed position of FIG. 1.

Rigidly secured in bottom section 14 to bottom wall 24 and extending upward from the bottom wall interior of the case are two spaced apart threaded studs 44 and 46 as shown in FIG. 2 which are used to retain the impression trays 47 which carry the upper and lower impressions made by the orthodontist in the patient's mouth, one such impression being indicated at 48. As is conventional, the impression trays 47 each have a hole 49 which, during transport is engaged onto threaded studs 44 and 46 after placement of a resilient spacer 50 and a washer 51 on the stud. A wing nut 52 is used to secure the impression and impression tray on to the stud and is tightened sufficient to somewhat compress resilient spacer 50. The impressions are essential for the laboratory to use in fabricating the gnathostomatic appliance.

Also essential for the laboratory is one or more measurements indicating the relative position of the upper and lower surfaces or the relative position of the upper and lower impressions. For this purpose it is conventional for the orthodontist to adjust in accordance with the patient's jaw configuration a face bow indicated generally at 53. Because the operation adjustments of the face bow are well understood and form no part of the invention, they will not be described in detail herein except to note that the face bow includes a base bar 54 which typically includes adjacent opposite extremities thereof threaded openings to mount the face bow on cooperating equipment in the office of the orthodontist. The presence of the threaded openings on base bar 54 are exploited in the present invention to firmly mount the face bow within case 12. For this purpose a pair of suitably spaced apart threaded studs 55 and 56 are rotatably supported in top wall 34 of cover section 16. The threaded studs pass through top wall 34 and are provided at the exterior surface of the case with knurled heads 55' and 56' respectively (FIG. 1) to enable engagement of the threads of studs 55 and 56 with the threads in the openings of opposite ends of the base bar 54. Thus when the parts of face bow 53 have been adjusted in accordance with the patient's jaw configuration the face bow is placed so that the holes in the opposite ends of base bar 54 register with threaded studs 55 and 56 after which the base bar is securely clamped to the inner surface of wall 34 by rotation of heads 55' and 56'. The face bow shown in FIG. 2, together with certain other numerical data, are sufficient for enabling the orthodontic laboratory to commence construction of the desired gnathostomatic appliance. However, the remaining structure of FIG. 2 will be described at this point and will be alluded to hereinbelow in conjunction with FIG. 3. Top wall 34 of cover section 16 is also provided with additional threaded studs 58 and 59 which are mounted in top wall 34 for rotation relative thereto as is the case with threaded studs 55 and 56. Threaded studs 58 and 59 extend exterior of cover section 16 at which they are provided respectively with enlarged knurled heads 58' and 59' (FIG. 1). Lower section 14 has extending upward from bottom wall 24 an additional pair of studs 60 and 61 which, as is the case with studs 44 and 46, are rigidly secured to the bottom wall. Finally, the interior of the case is provided with a spring clip 62 which is attached to side wall 26 of bottom section 14 and an identical clip directly opposite on the interior surface of side wall 28.

Referring now to FIG. 3, the case is seen in its condition upon return to the orthodontist for approval, if desired, before the gnathostomatic appliance is finally fabricated. In FIG. 3, face bow 53 is in place as described above after measurements have been taken from it by the orthodontic laboratory. The settings of the face bow have not been changed however to afford the orthodontist an opportunity to thoroughly appraise the accuracy of the laboratory work before approving final fabrication. Engaged in cover section 16 by threaded studs 58 and 59 are the set-up models 63 which are fabricated by the laboratory on the basis of impressions 48 and face bow registration. Such models are typically constructed of plaster like material with teeth reset in wax and with metal base members that define a threaded hole for engagement with threaded studs 58 and 59. Because the models are firmly retained within cover section 16, they are virtually impervious to breakage during transport.

Mounted in bottom section 14 is an articulator composed of a first element 64 and a second element 65. The articulator typically has various adjustments which are made by the laboratory on the basis of the adjustments communicated by the position of the parts of face bow 53 and other data supplied by the orthodontist. The articulator elements support model 63 in the relative position dictated by the patient's jaw configuration. For orienting the two elements of the articulator during testing and during fabrication of the gnathostomatic appliance a guide pin 66 cooperates with the articulator elements. The guide pin is retained in spring clip 62 and its counterpart on the interior surface of side panel 28. Articulator element 64 is retained within the case by engagement onto threaded stud 61, a washer 67 and a wing nut 68 being provided to retain the element within the case. It will be noted that studs 44 and 46 are positioned so as to avoid interference with articulator element 64. Articulator element 65 is retained within case 14 on threaded stud 60 by means of a washer 69 and a wing nut 70.

When the orthodontist receives the case containing the elements shown in FIG. 3, the orthodontist assembles the set-up models 63 onto articulator elements 64 and 65 and establishes the relative position of the articulator elements by means of guide pin 66. The orthodontist is thereby presented the set-up models 63 which will be used by the orthodontic laboratory in fabricating the gnathostomatic appliance and is thus enabled to determine that it precisely corresponds with the patient's jaw configuration and movements. When the orthodontist is satisfied that the work is accurate, the elements need only be reinserted into the transport as case 12 as shown in FIG. 3 and returned to the laboratory for final fabrication of the gnathostomatic appliance. The appliance, because it is constructed of pliable or rubber like material, is virtually unbreakable and it can be returned to the orthodontist within the case 12 or can be separately transported to the orthodontist. The transport case 12 of the present invention permits the elements shown in FIG. 3 and the finished gnathostomatic appliance to be returned to the orthodontist simultaneously so that the orthodontist can again check the appliance against the settings on the articulator and face bow. Thus at all times, the orthodontist is afforded an opportunity to evaluate the accuracy of the work done and communication of the necessary information between orthodontist and orthodontic laboratory is facilitated.

To recapitulate the operation of the embodiment of the invention shown in FIGS. 1 – 3, the orthodontist makes impressions 48 directly from the patient and sets the adjustments on the face bow 53 in a like manner. The orthodontist then installs these elements within the case (see FIG. 2) and transports the case to the laboratory. Because of the ruggedness of the case and the presence of hasp 22 and possibly a lock (not shown), the likelihood of damage to or loss of the apparatus is virtually eliminated. On receipt of the transport case 12 as shown in FIG. 2, the laboratory is in a position to fabricate set-up models 63. The laboratory is also in a position to set up the articulator elements 64 and 65 in accordance with the patient's jaw configuration and movements. The apparatus enumerated in the preceding sentence, together with face bow 53 are then installed in the case as shown in FIG. 3 and returned to the orthodontist who then has before him the exact equipment that the laboratory will use in the final fabrication of the gnathostomatic appliance. Therefore, it is virtually certain that the final product will conform to the expectations of the orthodontist. Thereupon the case, with the equipment shown in FIG. 3, is returned to the laboratory and the appliance is fabricated. With the equipment shown in FIG. 3, the appliance is returned to the orthodontist so that it can again be inspected before installation in the patient's mouth. Thus, the likelihood of error is reduced, the time of the orthodontist is conserved, and the time and convenience of the patient is optimized.

Figure 4:
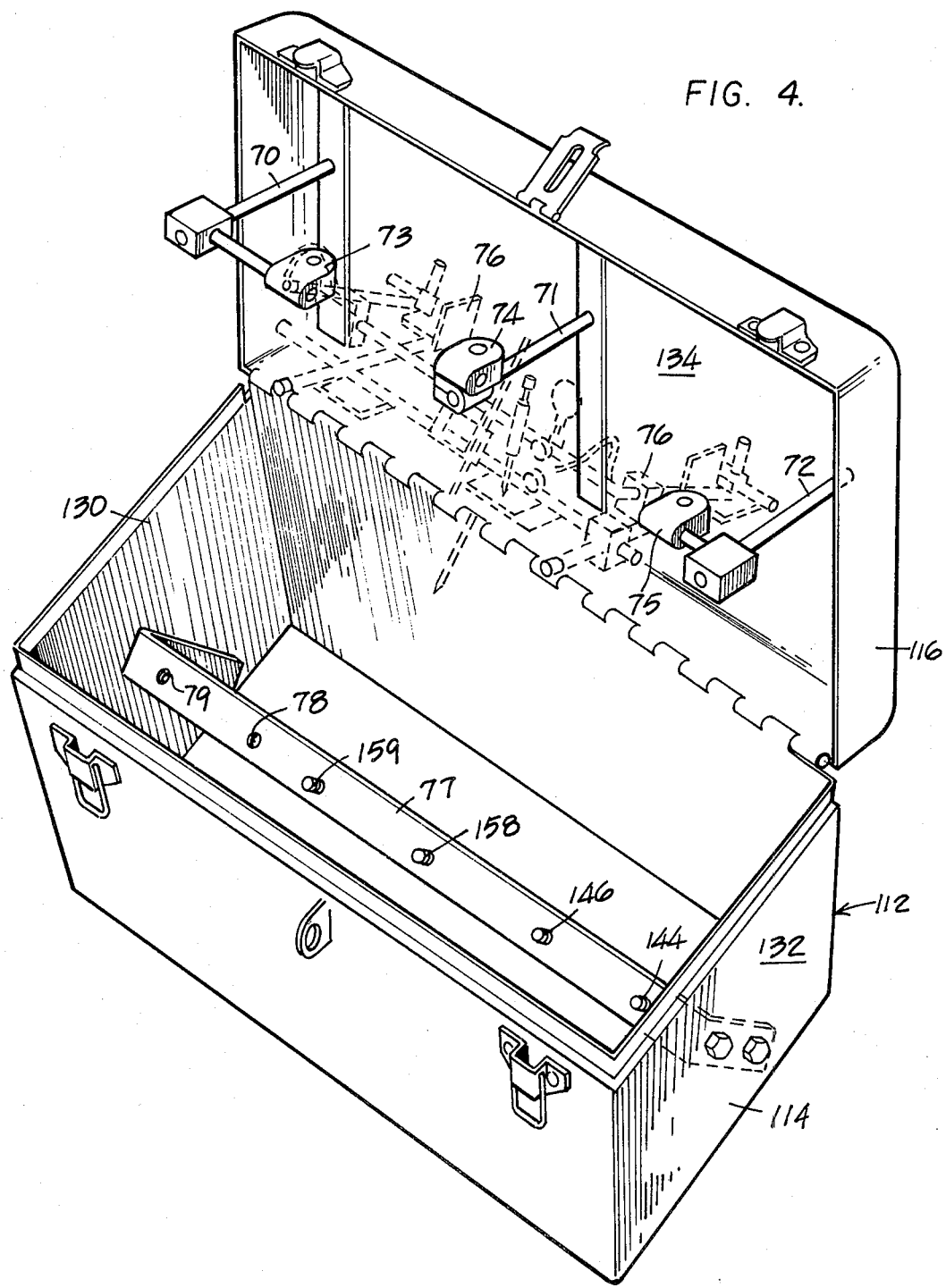
FIG. 4 is a perspective view of another embodiment of the transport case of the invention specifically adapted for transporting a pantograph.

Referring to FIG. 4 there is shown a case, the exterior of which is substantially identical to case 12 of FIGS. 1 – 3. Reference numerals greater by 100 than those used in describing the embodiment of FIGS. 1 – 3 are used in FIG. 4 to describe corresponding parts. That is to say, case 112 has a cover section 116 and a top wall 134 having extending therefrom a plurality of rods 70, 71 and 72. On the ends of the rods remote from top wall 134 are clamping assemblies 73, 74 and 75, respectively, which are constructed and arranged to secure to cover section 116 a pantograph 76 such as a Denar pantograph (shown in dotted outline), a measuring apparatus used by many practitioners. The pantograph 76 is adjusted in accordance with the patient's jaw structure and movements to afford the data necessary for the laboratory to make a proper gnathostomatic appliance. Use of the pantograph 76 in place of the face bow arrangement results in more accurate measurements because the actual mandibular movements of the patient are traced. Because the rods 70, 71 and 72 are rigid with cover section 116 and because the cover can be firmly secured to the lower section 114 of case 112, the pantograph 76 when secured by clamps 73, 74 and 75 will retain its settings during transport.

Spanning the end panels 130 and 132 of lower section 114 is a mounting bar 77. At spaced intervals along bar 77 are threaded studs and threaded receptacles such as those identified at 144, 146, 158, 159, 78 and 79. The studs are equivalent in function to studs 44, 46, 58 and 59 in FIGS. 1 – 3 in that they afford secure and removable attachment within case 112 of the impression trays 47 and the set-up models 63. The articulator elements 64 and 65 are positioned by means of screws which fit into threaded receptacles 78 and 79. The provision of bar 77 for supporting the threaded studs is but an alternative to the arrangement disclosed in FIGS. 1 – 3. The studs on bar 77 can either be rigid therewith or can be rotatably secured thereto. In the latter case, the studs are provided with knurled heads of the type identified at 55' and 56' in FIG. 1 to afford engagement of the threads of the stud with either nuts or complemental threaded openings in appliances to be secured within the case. Bar 77 is relatively narrow so as to afford access to the bottom surface of the bar and to the fastening elements carried thereon. Moreover, the bar is tilted, as shown in FIG. 4, to expedite access to such fastening elements as are on the lower surface of the bar.

Utilization of the embodiment of the invention shown in FIG. 4 is substantially identical to that described hereinabove in connection with FIGS. 1 – 3. The orthodontist takes upper and lower impressions as well as setting the pantograph apparatus 76 to accurately reflect the patient's jaw configuration and jaw movements. The pantograph is clamped to top section 116 by means of clamp assembly 73, 74 and 75 and the impression trays are secured on the threaded studs in cross bar 77. Thereupon the case is dispatched to the orthodontic laboratory. After the orthodontic laboratory has made upper and lower models corresponding to the impressions and has set the articulator in accordance with the settings in the pantograph apparatus, the pantograph apparatus is returned to the orthodontist in case 112 along with the articulator and the set-up models. The articulator and the models are secured within lower section 114 by engagement with the threaded studs on cross bar 77 or, if the lower section 114 is arranged as is section 14, by the procedure described hereinabove with respect to FIGS. 1 – 3. The orthodontist is then able to inspect the work and if it is in order can return to the orthodontic laboratory in the same case the models and the articulator in order that the gnathostomatic appliance can be completed. Thereupon the case and its contents, including the completed appliance, can be returned to the orthodontist.

Figure 5:
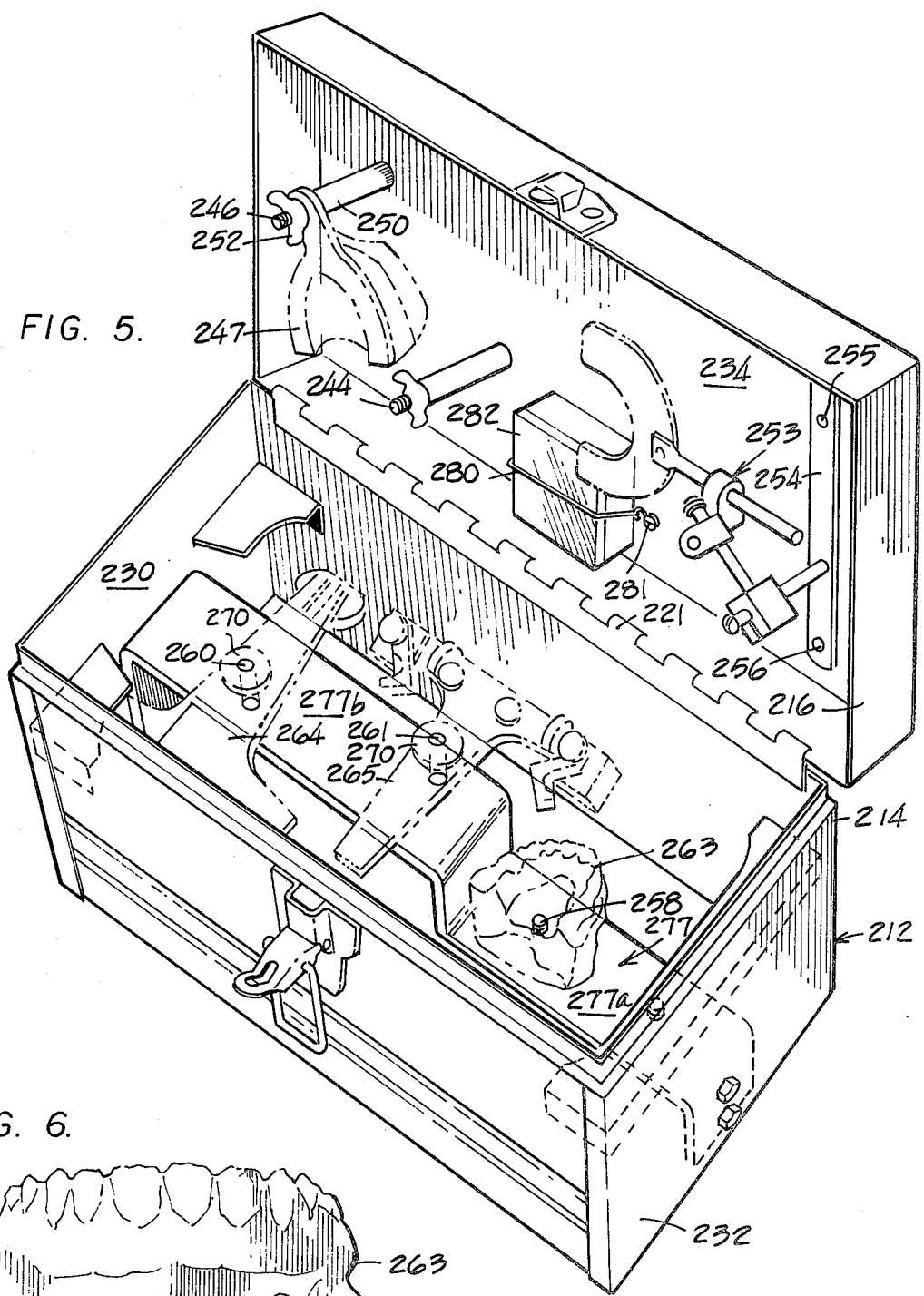
FIG. 5 is a perspective view of another embodiment of the transport case of the present invention.

Referring to FIG. 5 there is shown another case, the exterior of which is also similar to case 12 of FIGS. 1 – 3. Reference numerals greater by 200 than those used in describing the embodiment of FIGS. 1 – 3 are used in FIG. 5 to identify corresponding parts. Thus, case 212 has a cover section 216 and a top wall 234 which has extending therefrom spaced apart studs 255 and 256 to mount the face bow indicated generally at 253 and the base bar 254 thereof within the case 212. Also extending from top wall 34 are elongate spaced apart threaded studs 244 and 246 which are provided to retain impression trays 247 within the case. Resilient tubular spacers 250 and wing nuts 252 secure the impression tray 247 on the stud in spaced relation from the interior surface of top wall 234. The top wall is also provided with a resilient band 280, the ends of which are fixed to top wall 234, such as at 281. Band 280 is adapted to retain a box 282 in which the finished gnathostomatic appliance is placed by the laboratory when completed.

Figure 6:
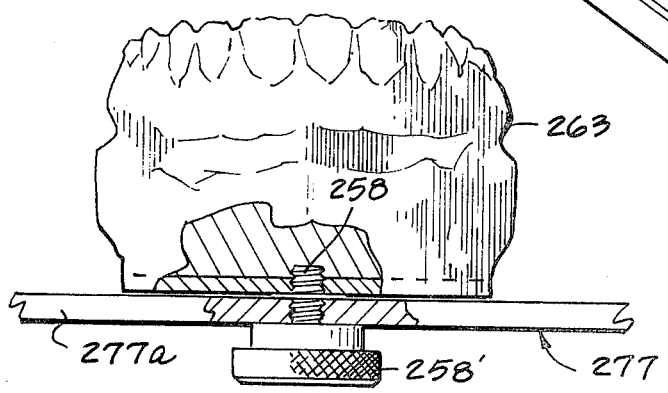
FIG. 6 is a side view showing a set-up model secured to the mounting bar.

Spanning side walls 230 and 232 of bottom section 214 is a rigid mounting bar 277. In addition to strengthening bottom case section 214 the mounting bar provides for secure retention of set-up models 263 and articulator elements 264 and 265. Mounting bar 277 has a lower level 277a in which there are two threaded studs 258 for engaging complemental threaded openings in set-up models 263. As seen in FIG. 5 the position of lower level 277a is such as to afford adequate space for the set-up models even though the parts of face bow 253 extend into bottom section 214 when the case is closed. The mounting bar also includes an upper level 277b extending upward from which there are two spaced apart threaded studs 260 and 261. Knurled nuts 270 are provided for engagement with threaded studs 260 and 261 so that articulator elements 264 and 265 can be securely mounted on the mounting bar. Level 277b of mounting bar 277 is elevated above wall 224 sufficient that the parts of articulator elements 264 and 265 can extend downward into bottom section 214, the width of mounting bar 277 being substantially less than the width of bottom section 214 to afford space for such portions of the articulator elements. The relatively narrow width of mounting bar 277 also permits entry of the user's hand to the underside of the bar such as is needed in engaging knob 258' of threaded stud 258. Because the method of using the embodiment of the invention shown in FIGS. 5 and 6 is believed apparent from the foregoing detailed description of the other embodiments, such method of operation will not be explained in detail here, it being sufficient to say that the embodiment of FIGS. 5 and 6 affords secure and convenient retention of the various parts for shipment between orthodontist and laboratory.

Thus it will be seen that the present invention provides a case that not only protects apparatus and appliances that are transported between orthodontist and orthodontic laboratory but permits the transport of measuring equipment without jeopardizing either the safety of measuring equipment of the settings contained therein. Accordingly the invention affords protection of valuable equipment, conservation of the orthodontist's time, and improved accuracy of the final results. The case, because its constituent parts are of extremely rugged construction has virtually an infinite life as contrasted with prior art packaging methods which employed disposable materials.

In addition, the transport case of the present invention can be used for any shipment of gnathological measuring instruments, such as between the general dental profession and the numerous dental laboratories associated therewith. The transport case can also be used by the general dental practitioner when involved in mouth reconstruction work.

Although three embodiments have been shown and described, it will be obvious that other adaptations and modifications can be made without departing from the true spirit and scope of the invention.

What is claimed is:

1. A transport case for gnathological apparatus comprising a rigid case having side walls, a top wall, and a bottom wall, said side walls defining a parting line and a hinge at the parting line on one of the side walls to afford access to the interior of the case, a plurality of threaded studs secured rigid with at least one of said case walls and projecting interior of the case, at least one impression tray with an impression thereon and having therein a hole remote from the impression suitable for positioning on a stud, a face bow with a base bar attached thereto having at least one hole therein suitable for positioning on a stud, means for securing said impression tray and face bow onto said studs, a rigid cross bar mounted within said case in spanning relation between two opposite side walls thereof, a set-up model having a threaded hole in the bottom thereof, an articulator having a first element and a second element with an aperture in each of said elements, and means for securing said set-up model and said articulator onto said rigid cross bar whereby said apparatus can be safely transported between orthodontist and laboratory.

2. A transport case according to claim 1 wherein at least one of said studs is secured in said case for rotation relative thereto, said one stud having a portion for affording a grip to permit rotation of said stud so as to threadedly engage an appliance in said case.

3. A transport case according to claim 1 including a resilient tubular spacer defining a central opening to afford passage of said threaded stud therethrough, said tubular spacer when compressed by engagement of an appliance engaged on last said threaded stud providing a cushioning effect between said appliance and said case.

4. A transport case according to claim 1 wherein at least two of said studs are secured to said top wall for rotation relative thereto and in spaced apart relation, last said studs each having a portion extending externally of said case for affording a grip to permit rotation of said stud so as to threadedly engage a model on each said stud within said case.

5. A transport case according to claim 1 wherein said cross bar has at least a first edge spaced apart from one of said side walls to afford access to the lower side of said cross bar.

6. A transport case according to claim 5 wherein said cross bar is tilted so that said first edge is higher than the opposite edge thereof.

7. A transport case according to claim 1 wherein said cross bar has at least two levels so as to afford attachment thereon of apparatus of different size.

8. A transport case for gnathological apparatus comprising a rigid case having side walls, a top wall, and a bottom wall, said side walls defining a parting line and a hinge at the parting line on one of the side walls to afford access to the interior of the case, a rigid cross bar mounted within said case in spanning relation between two opposite side walls and in tilted relationship thereto, at least one impression tray with an impression thereon and having therein a hole remote from the impression, a set-up model having a threaded hole in the bottom thereof, an articulator having a first element and a second element with an aperture in each of said elements, means for securing said set-up model, impression tray and articulator onto said rigid cross bar, and a plurality of elongate rods secured to one wall and projecting interior of the case, a clamp assembly fixed to the inner end of said rod, said clamp assemblies being adapted to removably secure a pantograph within the case whereby said apparatus can be safely transported between orthodontist and laboratory.

* * * * *